US010786170B2

(12) United States Patent
Warner et al.

(10) Patent No.: US 10,786,170 B2
(45) Date of Patent: Sep. 29, 2020

(54) ELECTROPHYSIOLOGY DATA ACQUISITION SYSTEM AND METHOD WITH DIFFERENTIATED EQUALIZATION DRIVE CIRCUITS

(71) Applicant: General Electric Company, Schenectady, NY (US)

(72) Inventors: Adrian F. Warner, Delafield, WI (US); Daniel R. Schneidewend, Menomonee Falls, WI (US); Timothy P. Stiemke, West Bend, WI (US); Rodger F. Schmit, West Bend, WI (US)

(73) Assignee: General Electric Company, Schenectady, NY (US)

( * ) Notice: Subject to any disclaimer, the term of this patent is extended or adjusted under 35 U.S.C. 154(b) by 190 days.

(21) Appl. No.: 16/019,247

(22) Filed: Jun. 26, 2018

(65) Prior Publication Data
US 2019/0387988 A1 Dec. 26, 2019

(51) Int. Cl.
*A61B 5/042* (2006.01)
*A61B 5/00* (2006.01)

(52) U.S. Cl.
CPC .......... *A61B 5/042* (2013.01); *A61B 5/6852* (2013.01); *A61B 5/7217* (2013.01)

(58) Field of Classification Search
CPC . A61B 5/7217; A61B 5/7203; A61B 5/04288; A61B 5/7225
USPC ........................................................ 600/513
See application file for complete search history.

(56) References Cited

U.S. PATENT DOCUMENTS

| 7,873,409 | B2 | 1/2011 | Schneidewend et al. |
| 8,554,311 | B2 | 10/2013 | Warner et al. |
| 9,078,578 | B2 | 7/2015 | Warner et al. |
| 9,591,981 | B2 | 3/2017 | Levin et al. |
| 2006/0136001 | A1 | 6/2006 | Ortega |

(Continued)

FOREIGN PATENT DOCUMENTS

| EP | 3097181 | 11/2016 |
| JP | 2014171826 A | 9/2014 |

(Continued)

OTHER PUBLICATIONS

European patent application No. 19182729.4 filed Jun. 26, 2019; Search Report dated Nov. 21, 2019; 8 pages.

(Continued)

*Primary Examiner* — Amanda K Hulbert
*Assistant Examiner* — Philip C Edwards (57) ABSTRACT

An electrophysiology data acquisition system that receives physiological signals from at least one catheter includes an amplifier and at least one noise reduction circuit operatively connected to the amplifier and configured to cancel interference in the physiological signals from the catheter. A drive selection circuit is controllable to connect any one of two or more available electrodes to the noise reduction circuit such that the connected electrode becomes an equalization drive electrode for the catheter. An equalization control module is executable on a processor and configured to select the equalization drive electrode from the two or more available electrodes and to control the drive selection circuit to connect the selected equalization drive electrode to the noise reduction circuit.

19 Claims, 5 Drawing Sheets

(56) References Cited

U.S. PATENT DOCUMENTS

2011/0166434 A1     7/2011   Gargiulo
2012/0323132 A1*   12/2012   Warner ................ A61B 5/7203
                                                                                     600/523

FOREIGN PATENT DOCUMENTS

WO         2015000500 A1    1/2015
WO         2017048421        3/2017

OTHER PUBLICATIONS

Japan 2014-171826, English translation of Abstract obtained from Espacenet.com, Apr. 14, 2020.

* cited by examiner

ELECTROPHYSIOLOGY DATA ACQUISITION SYSTEM AND METHOD WITH DIFFERENTIATED EQUALIZATION DRIVE CIRCUITS

BACKGROUND

The present disclosure generally relates to physiological data acquisition systems, and more particularly to data acquisition systems that connect to invasive catheters, such as for electrophysiology and/or invasive cardiology applications, having multiple differentiated and adjustable equalization drive circuits for noise reduction.

In order to properly and accurately diagnose cardiac conditions, it is important for the physician to have clear and clean cardiograms at his or her disposal. Therefore, an acquisition system for cardiac behavior must capture electrophysiological signals accurately, and such signals may be as small as six µV. These signals must be captured with very little noise, and displayed, stored and sent to other medical equipment in a real-time manner. These electrophysiological signals must be filtered in a number of ways and the captured data within the signals must reject artifacts caused by other equipment, such as by pacemaker or ablation devices.

Establishment and maintenance of minimized noise levels in electrophysiology systems in cardiac labs is a challenge. Sources of noise interference include environmental noise unrelated to the cardiac procedure, and noise resulting from procedural-related events and systems. Environmental noise includes, for example, ungrounded electrical extension cords, electrical sockets, equipment having a large electrical energy demand, etc. Procedural-related noise comes from, for example, ablation devices, pacemakers, and the various electronic systems associated with the various invasive catheters being simultaneously operated and the signal processing therefor.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, an electrophysiology data acquisition system that receives physiological signals from at least one catheter includes an amplifier and at least one noise reduction circuit operatively connected to the amplifier and configured to cancel interference in the physiological signals from the catheter. A drive selection circuit is controllable to connect any one or more of two or more available electrodes to the noise reduction circuit such that the connected electrode becomes an equalization drive electrode for the catheter. An equalization control module is executable on a processor and configured to select the equalization drive electrode from the two or more available electrodes and to control the drive selection circuit to connect the selected equalization drive electrode to the noise reduction circuit.

In another embodiment, an electrophysiology data acquisition system includes at least one catheter input module, wherein the catheter input module is configured to connect to at least one catheter to receive physiological signals therefrom. Each catheter input module includes an amplifier and at least one noise reduction circuit operatively connected to the amplifier and configured to cancel interference in the physiological signals from the catheter. The catheter input module further includes a drive selection circuit controllable to connect any of two or more available electrodes to the noise reduction circuit such that the connected electrode becomes an equalization drive electrode for the catheter. The system includes an equalization control module executable on a processor and configured to select the equalization drive electrode from two or more electrodes and to control the drive selection circuit to connect the selected equalization drive electrode to the noise reduction circuit.

In another embodiment, an electrophysiology data acquisition system includes a base unit operatively connected to receive physiological signals from each of at least two catheters. The base unit includes at least two amplifiers and at least two noise reduction circuits, wherein each noise reduction circuit is operatively connected to a respective one of the at least two amplifiers and is configured to cancel interference in the physiological signals from a respective one of the at least two catheters. The base unit further includes at least two drive selection circuits controllable to connect any of two or more electrodes to a respective one of the at least two noise reduction circuits such that each connected electrode becomes an equalization drive electrode for the respective one of the at least two catheters. The system further includes an equalization control module executable on a processor and configured to select a respective equalization drive electrode for each of the at least two catheters and to control each of the drive selection circuits accordingly.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Through their experimentation and research in the relevant field, the inventors have recognized that interference in electrophysiology signals, such as in invasive cardiology studies, has become an increasing problem. Namely, as electrophysiology data acquisition systems become more complex, as more and more catheters are added, each having their own functions and electronics, noise generated within the system has increased. Moreover, the inventors have recognized that such noise tends to be localized within the patient, and varies across different locals in the patient. Thus, current equalization, or grounding, schemes where all electrodes and electronics are referenced to a single reference point, such as a right leg electrode, are insufficient. The human body is generally a good resistor, and thus noise activity seen by electrodes in the heart may be very different than noise at the right leg electrode. In fact, noise seen in various chambers in the heart may even significantly differ from one another. For example, noise due to procedural activity in the right atrium may appear differently in signals recorded by devices in the right atrium than it appears in signals recorded by devices in other chambers of the heart, such as in the left atrium or left ventricle. For example, ablation occurring in the right atrium will create localized noise that appears most strongly in recordings by other catheter electrodes in the right atrium, and will appear less strongly and perhaps in a different frequency range in signals recorded by catheter electrodes in other chambers of the heart. The same ablation noise will appear differently still in distal surface electrodes, such as the right leg electrode typically used as the system reference electrode, or may not even be detectable at all. Accordingly, current noise reduction circuits, such as the standard right leg drive circuit, is sub-optimal for noise reduction, especially in modern electrophysiology data acquisition systems employing multiple catheters simultaneously.

Some current systems have addressed the lack of noise cancellation by the right leg drive circuit by utilizing aggressive signal processing to remove the noise. The inventors have recognized that such systems utilizing aggressive signal processing to remove noise are not ideal because noise commonly occurs in the same frequency ranges as the monitored physiological signals, and thus signal processing to remove noise also unknowingly removes features of the recorded physiological signal. Thus, the resulting physiological signals, and the parameters calculated therefrom, become less accurate.

Upon their recognition of the forgoing problems and challenges with noise cancellation in current electrophysiology data acquisition systems, the inventors developed the presently disclosed system and method that is able to select any of various electrodes as a local equalization drive electrode, such as for a particular catheter or group of catheters, to provide localized equalization and referencing, and thus superior interference cancellation. Accordingly, the inventors have developed an electrophysiology data acquisition system and method providing localized noise identification and removal, which allows post-acquisition filtering to be minimized or even eliminated.

To enable selection of a local equalization drive electrode for each catheter or group of catheters or other connected devices providing physiological signals, the system includes a drive selection circuit controllable to connect at least one of two or more available electrodes to a noise reduction circuit such that the connected electrode becomes the equalization drive electrode and the connected noise reduction circuit becomes the equalization drive circuit connected to the amplifier amplifying the physiological signals. Thereby, the drive selection circuit can select the frequency response of the feedback loop, defining the transfer function of the feedback circuit that allows interference cancellation. Additionally, the drive selection circuit may be configured to select between one or more available noise reduction circuits, such as to select between two or more active or passive circuits having various configurations and frequency responses. Thus, the drive selection circuit may be controlled to tune the noise cancellation performance based on the specific environment within the patient and the localized activity.

As used herein "active" circuits are those that contain transistors, such as power supplies, amplifiers, or converters, "passive" circuits refer to circuits containing only passive components, such as resistors, capacitors, and inductors. Each drive selection circuit may be controllable to select at least one of passive or active circuits that are each tuned to provide particular noise cancellation performance. In certain embodiments, the system may also include noise cancellation circuits that are modifiable to adjust the response characteristics of the particular circuit, such as by controlling switches within the noise reduction circuit to add or remove elements to the modifiable noise reduction circuit. Accordingly, the system provides an equalization drive circuit that can be modified throughout a procedure to provide a reference strategy that addresses specific local noise conditions seen in a catheter or group of catheters or connected electrodes.

Some existing systems provide adjustable noise reduction circuits, such as U.S. Pat. No. 9,078,578 disclosing an adjustable right leg drive circuit for use in surface ECG systems, which is hereby incorporated by reference in its entirety. However, such systems are inadequate for addressing the disparate noise issues seen in current electrophysiology data acquisition systems utilized in cardio catheterization procedures because they provide a single noise cancellation configuration for all electronics across the entire system. As described above, the inventors have recognized that providing a single noise cancellation reference is inadequate for addressing the varied noise conditions seen across the system.

In developing the disclosed solution allowing selection and modification of local equalization drive electrodes for each catheter or group of catheters, the inventors recognized and addressed particular problems relating to the creation of an electrophysiology data acquisition system having multiple applied parts. As will be known by a person having ordinary skill in the art, patient-connected electronics are floating, isolated from earth ground for patient protection in the event of a fault condition. Current regulations require four kilovolts of isolation between the patient and earth ground. Thus, current data acquisition systems for electrophysiology are generally referenced together with the patient, where the patient and all electronics are referenced together as a single applied part. The inventors have created an electrophysiology data acquisition system having multiple applied parts, where each individual applied part has its own localized reference point to the patient, and where each applied part floats individually and is sufficiently isolated from the other applied parts comprising part of the same system. Thus, each catheter or group of catheters or other devices may comprise its own applied part, each having its own programmable and controllable equalization drive circuit comprising its own noise reduction circuit and equalization drive electrode.

The equalization drive circuit is customizable by controlling the drive selection circuit to select one or more of multiple available electrodes as the equalization drive electrode, and may also be configured to select or modify an appropriate noise reduction circuit. The drive selection circuit is controlled by an equalization control module, which is a software module configured to control the drive selection circuit in order to adjust the equalization drive circuit.

The equalization control module may be configured to control the drive selection circuit based on any one or more of catheter configuration information, such as catheter type and/or catheter location in the patient, and a noise profile in the physiological signals from the catheter. The noise profile may include, for example, a frequency profile of the noise and/or a signal to noise ratio. Other important criteria for selecting the drive selection circuit could include knowledge of current pacing or ablation activity, or the presence of third party devices such as mapping systems. The system typically has this knowledge via existing third party device integration. Thereby, the equalization control module can control multiple different local equalization drive circuits based on the noise seen locally by the connected electronics within each applied part.

Figure 1:
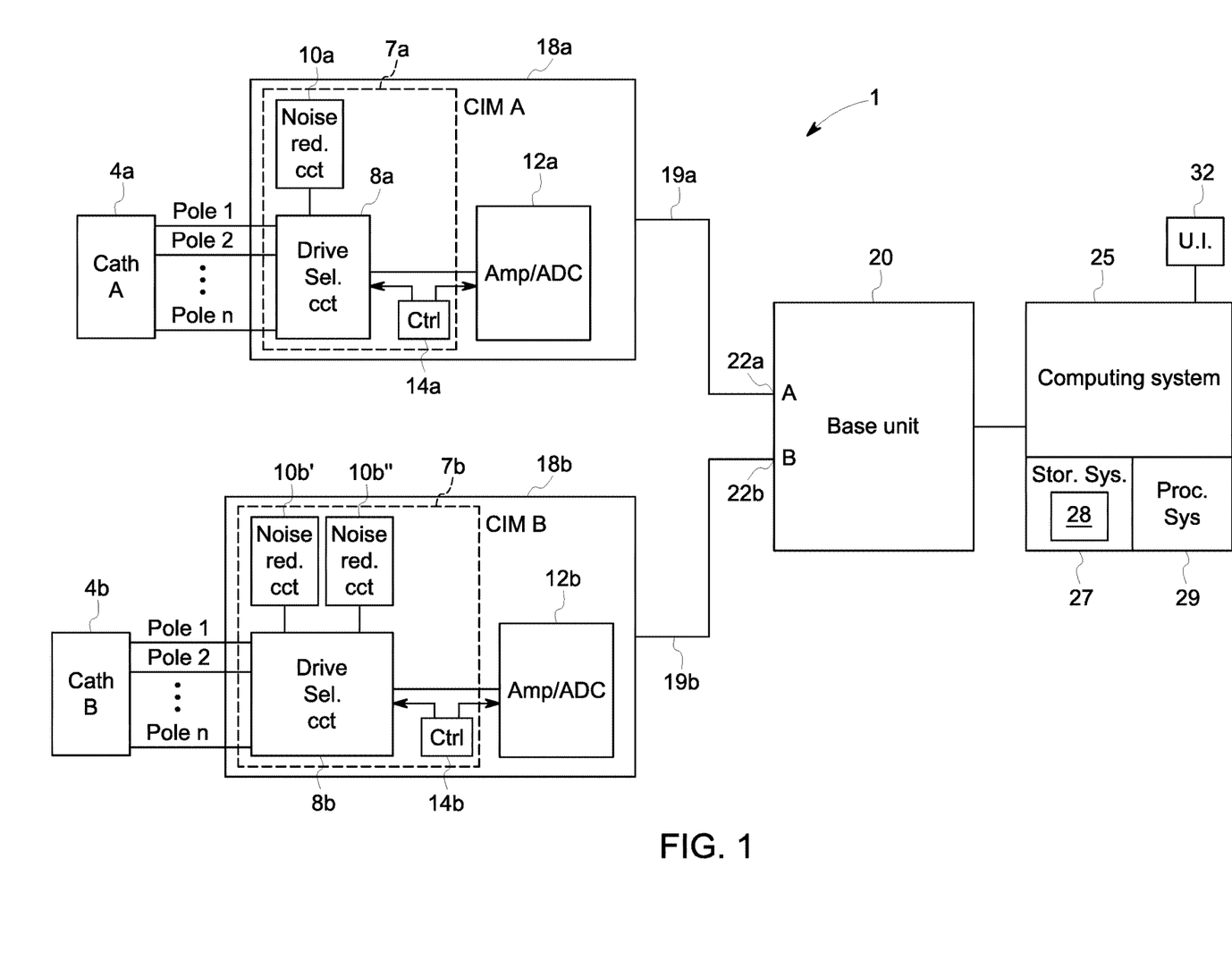
FIG. 1 is a schematic diagram illustrating an exemplary electrophysiology data acquisition system having multiple noise reduction circuits in accordance with the present disclosure.
Figure 2:
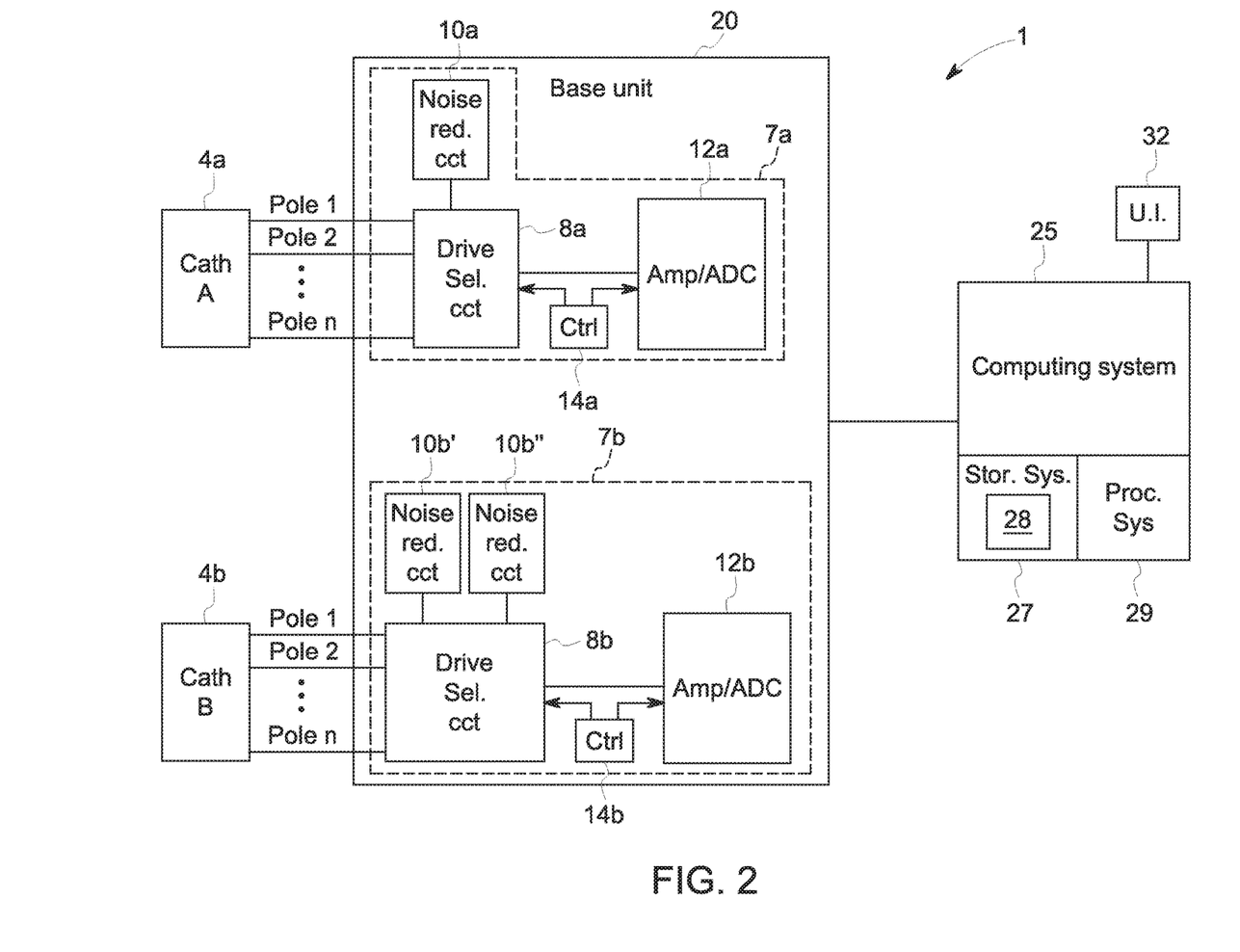
FIG. 2 is schematic diagram of another embodiment of an electrophysiology data acquisition system having multiple noise reduction circuits in accordance with the present disclosure.

FIGS. 1 and 2 depict exemplary electrophysiology data acquisition systems 1 having multiple equalization drive circuits with selectable equalization drive electrodes. In FIG. 1, the electrophysiology data acquisition system 1 includes two catheter input modules 18a and 18b connected to a base unit 20. Each catheter input module (CIM) 18a, 18b connects to a respective one or more catheters 4a, 4b and collects physiological signals therefrom. The physiological signals from the catheters 4a, 4b are then provided from the respective CIM 18a, 18b to the base unit 20. Depending on the configuration of the CIM 18, the physiological signals may be digitized within the CIM 18 and provided to the base unit 20 in digital form, or may be provided from the CIM 18 to the base unit 20 in analogue form and may be digitized upon receipt at the base unit 20. Digitized physiological signals are provided from the base unit 20 to the computing system 25 comprising software for displaying, storing, and/or further processing the physiological signals and for controlling the system 1.

A user interface 32 is communicatively connected to the computing system 25, wherein the computing system 25 is configured to provide various display configurations to a clinician via the user interface 32, such as to graphically or numerically depict the physiological signals recorded by the catheters 4a, 4b and/or other sensor data collected by the catheters. Additionally, the computing system 25 is configured to display system information and display control options to the clinician via the user interface 32, and to accept control instructions by the clinician in order to control the catheters 4a, 4b and/or associated system components, including the various drive selection circuits 8a, 8b. To facilitate control of the drive selection circuits 8a, 8b the computing system includes an equalization control module 28 stored within the storage system 27 and executable by the processing system 29 within the computing system 25.

In various embodiments, the equalization drive circuits 7a, 7b may be contained at various locations within the system 17, including at one or more of the CIMs 18 and/or at the base unit 20. In FIG. 1, each CIM 18a, 18b has its own equalization drive circuit 7a, 7b, and thus each CIM acts as its own applied part with its own equalization, grounding reference. Each equalization drive circuit 7a, 7b has a respective drive selection circuit 8a, 8b and a respective one or more noise reduction circuits 10a, 10b. A controller 14a, 14b is also provided to control and actuate the drive selection circuit 8a, 8b in accordance with instructions from the equalization control module 28. Accordingly, the system 1 is configured such that control instructions are provided from the computing system 25 to the local controller 14a, 14b for each drive selection circuit 8a, 8b, which may be by any wired or wireless means. In the depicted embodiment, for example, the control instructions generated by the equalization control module 28 are provided from the computing system 25 through the base unit 20 and through the connection between the base unit 20 and the respective CIM 18a, 18b. Each CIM 18a, 18b may be connected to the base unit 20 by any of various wired or wireless means. As is standard in available systems, each CIM 18a, 18b may be connected to the base unit 20 by a connection cable 19a, 19b terminating at a connector received at a CIM connection port 22 in the base unit 20. The connection cable 19a, 19b provides galvanic connection between the CIM 18a, 18b and the respective CIM connection port 22a, 22b for transmission of the physiological signals from the CIM 18a, 18b to the base unit 20, and control signals from the base unit 20 to the respective CIM 18a, 18b. Depending on the configuration of the respective CIM 18a, 18b and whether it digitizes the physiological signals or provides analogue signals, the connection cable 19a, 19b and CIM connection port 22a, 22b may configured to transmit and receive digitized physiological signals or analogue physiological signals.

In the depicted embodiment, each CIM 18a, 18b has a respective amplifier and analogue-to-digital converter (ADC) unit 12a, 12b. Thus, each CIM 18a, 18b provides digitized physiological signals to the base unit 20. In other embodiments, one or more of the CIMs 18a, 18b may not contain any digitization circuitry and may provide analogue physiological signals to the base unit 20. In such embodiments, the equalization drive circuitry 7 may be provided in the base unit 20, such as to receive signals from the respective CIM connection port 22 to process and digitize the physiological signals. In other embodiments, the system 1 may not include CIMs, and the catheters 4a, 4b may be connected directly to the base unit 20. In such embodiments, the equalization drive circuits 7a, 7b are likewise contained in the base unit 20. Thus, the base unit 20 may comprise multiple equalization drive circuits 7a, 7b, and thus may be divided into multiple applied parts.

Figure 3:
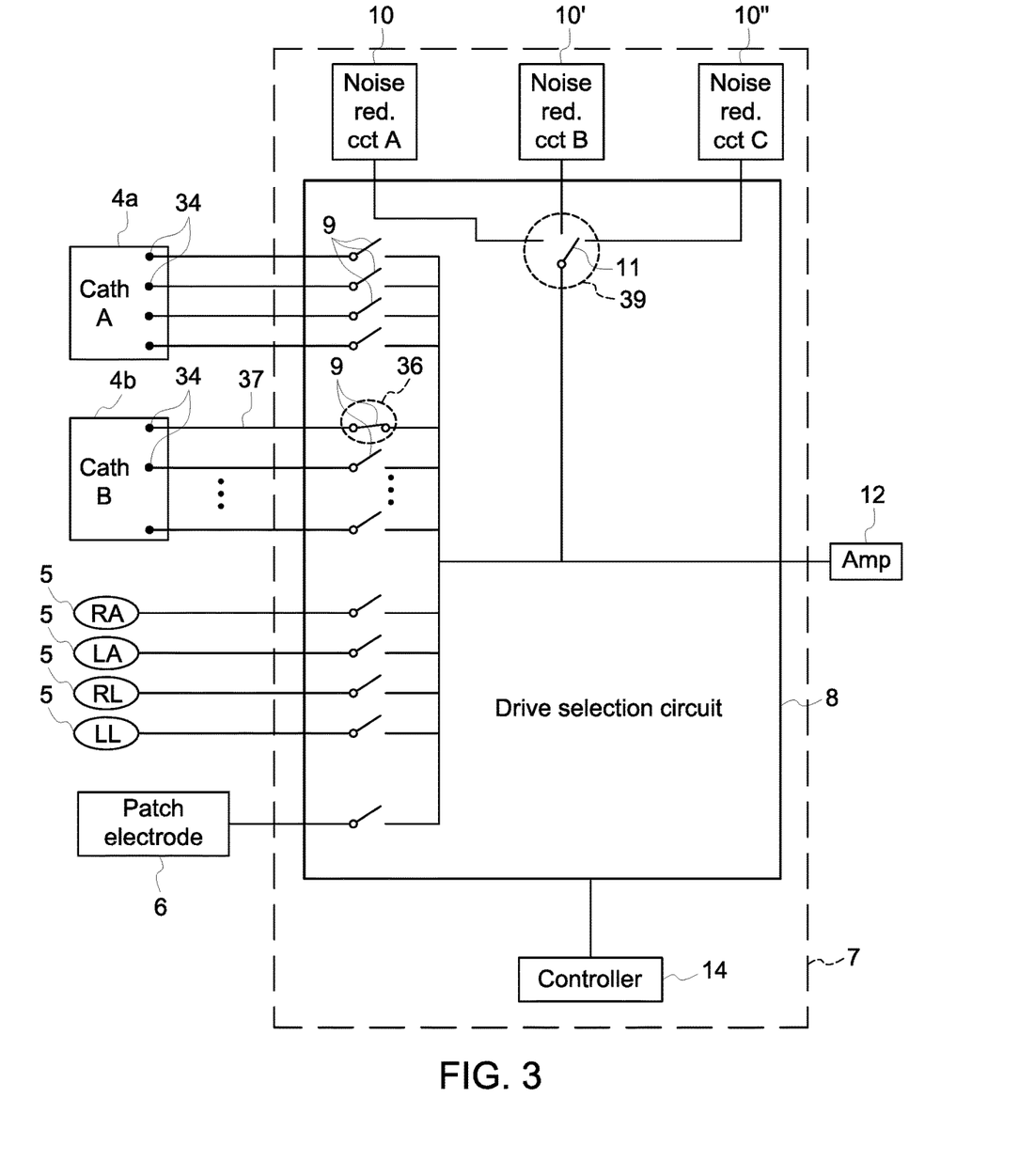
FIG. 3 is a schematic diagram of an exemplary drive selection circuit controllable to select from multiple available electrodes to become the equalization drive electrode and to select between multiple noise reduction circuits for connection to the equalization drive electrode in order cancel interference in the physiological signals.

FIG. 3 depicts an exemplary equalization drive circuit 7 having a drive selection circuit 8 connected to four devices, including two different catheters 4a, 4b, a set of ECG electrodes 5, and a patch electrode 6. The drive selection circuit 8 is configured to connect any of multiple available electrodes on the various devices 4, 5, 6 to a noise reduction circuit such that the connected electrode becomes an equalization drive electrode. In certain embodiments, equalization drive electrode may comprise multiple selected electrodes, which may be any subset of the available electrodes that are combined to form the reference (e.g., similar to a Wilson Central Terminal). In the schematic diagram of this depicted embodiment, the drive selection circuit 8 may select any catheter electrode 34 of either the first or second catheters 4a, 4b, any of the ECG electrodes 5, or the patch electrode 6 of the equalization drive electrode. In the depicted embodiment, the drive selection circuit 8 is schematically represented as a set of multiple switches 9, one for each electrode connection, where one switch gets closed to connect the respective electrode to the noise reduction circuit. In the example at FIG. 3, the switch 9 at position 36 is closed to select the first electrode of catheter 4b as the equalization drive electrode 37 for the connected devices, which include both catheters 4a, 4b and the ECG electrodes 5. For instance, the electrode selected from catheter 4b may be, for example, an electrode on a sheath of the catheter 4b electrically connecting to the tissue at the entrance point of the catheter 4b to the patient's body. To provide another example, the electrode from catheter 4b selected as the equalization drive electrode 37 may be the nipple electrode on a basket catheter. In certain embodiments, two or more of the available electrodes could be selected as the equalization drive electrodes, and would be thus joined to the circuit through a means such as electrical summation and averaging. For example, poles 1 and 2 in FIG. 4C could be selected and joined in this way.

In other embodiments, the ECG electrodes 5 may be connected to their own equalization drive circuit 7, such as connected to a different CIM having its own equalization drive circuit 7, which would be separate and isolated from the equalization drive circuit for the catheters 4a, 4b. Alternatively or additionally, the catheters 4a, 4b may each be isolated and provided their own equalization drive circuit 7.

Figure 4A:
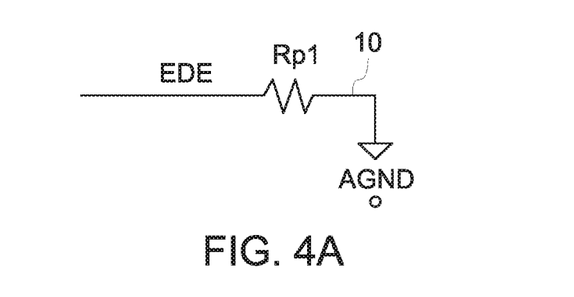
FIGS. 4A-4C are circuit diagrams representing various exemplary noise reduction circuits that could be utilized in accordance with the systems and methods of the present disclosure.
Figure 4B:
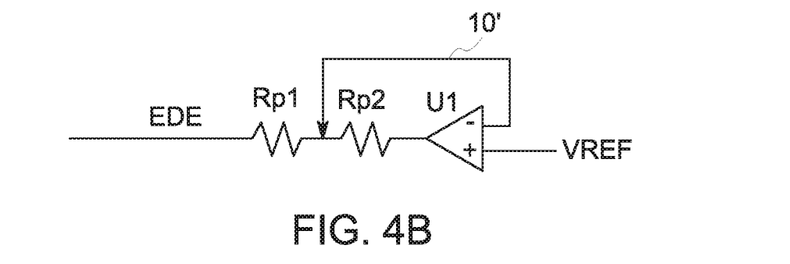
Figure 4C:
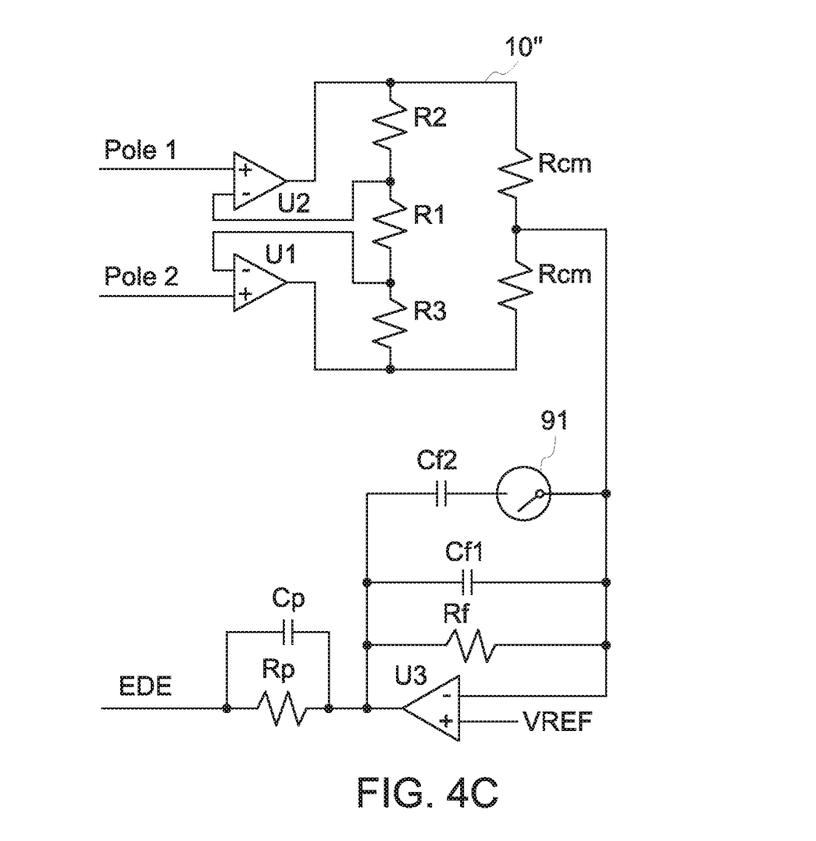

In the depicted embodiment, the equalization drive circuit 7 includes multiple noise reduction circuits selected by switch 11. In the depicted embodiment, the equalization drive circuit 7 includes three selectable noise reduction circuits 10, 10', 10". Each noise reduction circuit 10, 10', 10" provides a different frequency response. In the depicted example, switch 11 is in position 39 to select the third noise reduction circuit 10", which is connected to the equalization drive electrode(s) 37 to create the equalization drive circuit 7 that provides a reference for amplification of the physiological signals by the amplifier 12. FIGS. 4A-4C depict exemplary noise reduction circuits 10, 10', 10". Each noise reduction circuit is connected to the selected equalization drive electrode (EDE). FIG. 4A depicts a passive noise reduction circuit 10. FIG. 4B is a diagram of an active noise reduction circuit 10', and FIG. 4C is an example of an active noise reduction circuit 10" with selectable response characteristics which are adjusted by opening or closing switch 41 to change the frequency response of the circuit 10".

In various embodiments, the drive selection circuit 8 may comprise any number and arrangement of switches or relays controllable to connect and disconnect the relevant electrodes 34 and/or noise reduction circuits 10 from the equalization drive circuit 7. For example, the drive selection circuit 8 may comprise one or more low impedance solid-state switches, photoMOS relays, or electro-mechanical relays. In other embodiments, other switching devices may be utilized. In certain examples, the electrodes available as equalization drive electrodes may be more limited such that only certain electrodes, such as electrodes connected to designated positions on a CIM for example, may be connectable via the switches 9 to the noise reduction circuit 10.

Controller 14 controls the drive selection circuit 8 to select the equalization drive electrode 37 and to select and/or modify a noise reduction circuit in order to respond to the local noise level recorded in the physiological signals. The controller 14 is responsive to control instructions by the equalization control module 28. The equalization control module may be configured to receive, for example, catheter configuration information for each catheter connected to each drive selection circuit 8 and to select the equalization drive electrode 37 based thereon. Catheter configuration information may include, for example, a catheter location in the patient, such as which cardiac chamber the catheter is located in. Alternatively or additionally, catheter configuration information may include a catheter type, such as whether the catheter is an ablation catheter or an electrophysiology catheter, and the electrode configuration, including the number of poles, catheter shape, and poll arrangement, etc. To provide just one explanatory example, the catheter type may indicate that the catheter 4 is a basket catheter. The equalization control module 28 can utilize that information to select the nipple electrode of the basket catheter as the equalization drive electrode 37. To provide another example, the catheter configuration information may indicate that the respective catheter 4 is a catheter in the high right atrium and is positioned measure the first activation point that starts the electrical conduction of a heartbeat. In such a scenario, the equalization control module may be programmed to select an electrode on the HRA catheter as the equalization drive electrode 37. Depending on the system configuration, for example, the selection of the HRA catheter may be for a group of catheters in or near the right atrium.

Alternatively or additionally, the equalization control module 28 may be configured to receive and analyze the physiological signals recorded by each catheter or group of catheters, and analyze the physiological signals to determine a noise profile. As also discussed above, the noise profile may include a frequency range of the noise in the physiological signals from the catheter or group of catheters, and/or a signal to noise ratio of the signals. Based on the catheter configuration information and the noise level information, the equalization control module 28 can select the equalization drive electrode and, in certain embodiments, fine tune the noise reduction circuit 10 to best address the interference that is occurring within the system.

Figure 5:
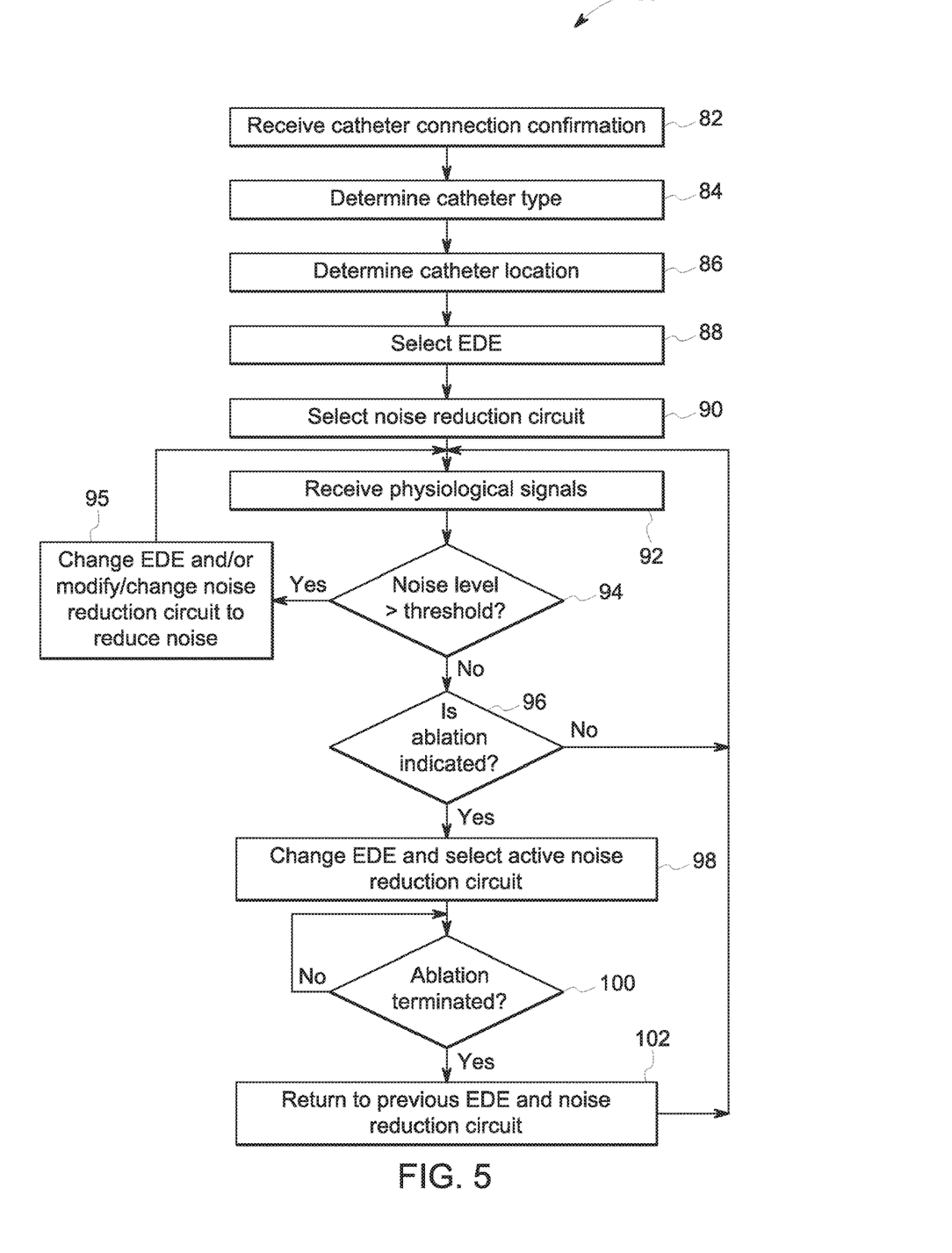
FIG. 5 is a flow chart illustrating an exemplary method of controlling an electrophysiology data acquisition system in accordance with the present disclosure.

FIG. 5 depicts one embodiment of a method 80. Catheter connection confirmation is received at step 82 confirming that a new catheter has been connected to the system 1. A catheter type is determined at step 84. In certain embodiments, the equalization control module 28 may determine the catheter type based on an identifier communicated and received from the respective catheter. In other embodiments, the catheter type may be provided as input through the user interface 32 by a clinician. In still other embodiments, the equalization control module 28 may identify the catheter type based on the physiological signals received therefrom, such as based on the number of channels received and the morphology of the physiological signals. The catheter location is determined at step 86, which may again be based on identification information communicated by the catheter 4 or based on clinician input. In other embodiments, the equalization control module 28 may be configured to determine the catheter location based on the physiological signals received therefrom, such as by comparing the timing of the physiological signals to other physiological signals received, such as from other catheters, or from surface ECG electrodes. Alternatively or additionally, the equalization control module 28 may be configured to determine the catheter location utilizing imaging modalities that can visualize and detect catheter location.

An initial equalization drive electrode 37 may then be selected as step 88 based on the catheter type and the catheter location. A noise reduction circuit is selected at step 90, also based on the catheter type and catheter location. Physiological signals are received at step 92 and analyzed at step 94 to determine whether a noise level, such as a signal to noise ratio, exceeds a threshold noise level. In certain embodiments, step 94 may also assess a frequency profile of the noise. If the noise level exceeds the threshold, then the equalization control module 28 adjusts the equalization drive circuit 7 at step 95, which may include selecting a different equalization drive electrode 37 from the other available electrodes, modifying the noise reduction circuit, and/or selecting a different noise reduction circuit.

Assuming that the noise level does not exceed the threshold at step 94, the system may be configured to determine whether an ablation is imminent, which is represented at step 96. For example, the equalization control module may know, such as based on instructions provided or queued up in other software modules within the computing system 25, that an ablation will soon occur. If so, the equalization control module 28 may be configured to adjust the equalization drive circuit 7 for catheters in the vicinities of the ablation that are likely to see excessive noise from the ablation activity (step 98). For example, the equalization control module 28 may change the equalization drive electrode 37 to a more localized drive electrode, such as on the respective catheter, and may select an active noise reduction circuit. The adjusted equalization drive circuit 7 may be maintained in the form selected at step 98 until the equalization control module 28 determines that the ablation is ended at step 100. Upon termination of the ablation, step 102 may be executed by the equalization control module 28 to return the equalization drive circuit 7 to its previous setting prior to the start of ablation.

The systems and methods described herein may be implemented with one or more computer programs executed by one or more processors of the processing system 25, which may all operate as part of a single computing system 25. The computer programs include processor-executable instructions stored within the storage system 27, which includes a non-transitory tangible computer readable medium. The computer programs may also include stored data stored in the storage system 27. Non-limiting examples of the non-transitory tangible computer readable medium are nonvolatile memory, magnetic storage, and optical storage This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. An electrophysiology data acquisition system that receives physiologic signals from at least one catheter, the system comprising:
   an amplifier;
   at least one noise reduction circuit operatively connected to the amplifier and configured to cancel interference in the physiological signals from the at least one catheter;
   a drive selection circuit controllable to connect any one of two or more available electrodes to the noise reduction circuit such that the connected electrode becomes an equalization drive electrode for the at least one catheter; and
   an equalization control module executable on a processor and configured to select the equalization drive electrode from the two or more available electrodes and to control the drive selection circuit to connect the selected equalization drive electrode to the noise reduction circuit;
   wherein the noise reduction circuit is modifiable to adjust a frequency response of the noise reduction circuit; and
   wherein the equalization control module is further configured to control the noise reduction circuit to adjust the frequency response thereof based on at least one of a noise profile in the physiological signals from the catheter, a catheter location in the patient, and a catheter type.

2. The system of claim 1, wherein the two or more available electrodes include at least one electrode on the at least one catheter or at least one electrode on a sheath of the at least one catheter.

3. The system of claim 2, wherein the two or more available electrodes further include at least one surface ECG electrode on a patient or a patch electrode on the patient.

4. The system of claim 1, wherein the drive selection circuit is controllable to connect any subset of the two or more available electrodes to the noise reduction circuit such that the connected electrodes become the equalization drive electrodes for the at least one catheter.

5. The system of claim 1, wherein the equalization control module is further configured to:
   receive catheter configuration information for the at least one catheter; and
   select the equalization drive electrode based on the catheter configuration information.

6. The system of claim 5, wherein the catheter configuration information includes at least one of a catheter location in a patient and a catheter type.

7. The system of claim 1, wherein the equalization control module is further configured to:
   determine a noise profile in the physiological signals from the catheter;
   select the equalization drive electrode based on the noise profile.

8. The system of claim 1, further comprising a plurality of noise reduction circuits, each operatively connectable to the amplifier to cancel interference in the physiological signals from the at least one catheter;
   wherein the drive selection circuit is further controllable to connect any of the plurality of noise reduction circuits to the equalization drive electrode and the amplifier; and
   wherein the equalization control module is further configured to select one of the plurality of noise reduction circuits and control the drive selection circuit to connect the selected noise reduction circuit to the equalization drive electrode and the amplifier.

9. The system of claim 8, wherein the plurality of noise reduction circuits include at least one passive noise reduction circuit and at least one active noise reduction circuit.

10. The system of claim 1, configured to further receive physiologic signals from at least a second catheter having at least two electrodes, the system further comprising:
    a second amplifier;
    at least a second noise reduction circuit operatively connected to the second amplifier and configured to cancel interference in the physiological signals from the second catheter;
    a second drive selection circuit controllable to connect any one of two or more available electrodes to the second noise reduction circuit such that the connected electrode becomes an equalization drive electrode for the second catheter; and
    wherein the equalization control module is further configured to select the equalization drive electrode for the second catheter from the two or more available electrodes and to control the second drive selection circuit to connect the selected equalization drive electrode for the second catheter to the second noise reduction circuit.

11. The system of claim 10, further comprising:
at least two catheter input modules, each configured to connect to a respective one of the at least two catheters to receive the physiological signals therefrom;
wherein each catheter input module includes a respective noise reduction circuit and drive selection circuit;
a base unit operatively connected to both of the at least two catheter input modules to receive the physiological signals therefrom;
a computing system communicatively connected to the base unit and each of the at least two catheter input modules, the computing system configured to store and execute the equalization control module controlling all of the respective drive selection circuits.

12. The system of claim 10, further comprising:
a base unit operatively connected to receive the physiological signals from each of the at least two catheters, the base unit comprising at least two noise reduction circuits and at least two drive selection circuits, wherein each of the at least two noise reduction circuits and the at least two drive selection circuits is paired with a respective one of the at least two catheters; and
a computing system communicatively connected to the base unit, the computing system configured to store and execute the equalization control module controlling the respective drive selection circuits.

13. A electrophysiology data acquisition system comprising:
at least one catheter input module, wherein the catheter input module is configured to connect to at least one catheter to receive physiologic signals therefrom, each catheter input module including:
an amplifier;
at least one noise reduction circuit operatively connected to the amplifier and configured to cancel interference in the physiological signals from the at least one catheter;
a drive selection circuit controllable to connect any of two or more available electrodes to the noise reduction circuit such that the connected electrode becomes an equalization drive electrode for the catheter; and
an equalization control module executable on a processor and configured to select the equalization drive electrode from the two or more available electrodes and to control the drive selection circuit to connect the selected equalization drive electrode to the noise reduction circuit;
the system further comprising a plurality of noise reduction circuits, each operatively connectable to the amplifier to cancel interference in the physiological signals from the at least one catheter;
wherein the drive selection circuit is further controllable to connect any of the plurality of noise reduction circuits to the equalization drive electrode and the amplifier; and
wherein the equalization control module is further configured to select one of the plurality of noise reduction circuits and control the drive selection circuit to connect the selected noise reduction circuit to the equalization drive electrode and the amplifier.

14. The system of claim 13, wherein the two or more available electrodes include at least one electrode on the at least one catheter or at least one electrode on a sheath of the at least one catheter.

15. The system of claim 13, wherein the equalization control module is further configured to select the equalization drive electrode based on at least one of catheter configuration information for the at least one catheter and a noise profile in the physiological signals from the at least one catheter.

16. A electrophysiology data acquisition system comprising:
a base unit operatively connected to receive physiological signals from each of at least two catheters, the base unit including:
at least two amplifiers;
at least two noise reduction circuits, wherein each noise reduction circuit is operatively connected to a respective one of the at least two amplifiers and is configured to cancel interference in the physiological signals from a respective one of the at least two catheters;
at least two drive selection circuits controllable to connect any of two or more available electrodes to a respective one of the at least two noise reduction circuits such that each connected electrode becomes an equalization drive electrode for the respective one of the at least two catheters; and
an equalization control module executable on a processor and configured to select a respective equalization drive electrode for each of the at least two catheters and to control each of the drive selection circuits accordingly;
wherein the equalization control module is further configured to select the equalization drive electrode for the second catheter from the two or more available electrodes and to control the second drive selection circuit to connect the selected equalization drive electrode for the second catheter to the second noise reduction circuit.

17. The system of claim 16, wherein the two or more available electrodes for a first one of the at least two catheters includes at least one electrode on a first catheter, and wherein the two or more available electrodes for a second one of the at least two catheters includes at least one electrode on a second catheter.

18. The system of claim 16, wherein the two or more available electrodes for one of the at least two catheters include an electrode on a sheath of the respective catheter.

19. The system of claim 16, wherein the equalization control module is further configured to select the respective equalization drive electrode for each of the at least two catheters based on at least one of catheter configuration information for the respective catheter and a noise profile in the physiological signals from the respective catheter.

* * * * *